US00PP27707P3

(12) United States Plant Patent
Olesen

(10) Patent No.: US PP27,707 P3
(45) Date of Patent: Feb. 28, 2017

(54) CLIMBING ROSE PLANT NAMED 'POULCY016'

(50) Latin Name: ***Rosa* hybrid**
Varietal Denomination: Poulcy016

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 183 days.

(21) Appl. No.: 14/121,296

(22) Filed: Aug. 15, 2014

(65) Prior Publication Data

US 2016/0050805 P1 Feb. 18, 2016

(51) Int. Cl.
*A01H 5/02* (2006.01)

(52) U.S. Cl.
USPC ..... Plt./115

(58) Field of Classification Search
USPC ..... Plt./115
See application file for complete search history.

*Primary Examiner* — Keith Robinson

(57) ABSTRACT

A new garden rose plant of the Climbing class which has abundant, red flowers and attractive foliage. This new and distinct variety has shown to be uniform and stable in the resulting generations from asexual propagation.

2 Drawing Sheets

Botanical designation: *Rosa* hybrid.
Variety denomination: 'Poulcy016'.

SUMMARY OF THE INVENTION

The present invention constitutes a new and distinct variety of garden rose plant which originated from a controlled crossing between the female seed parent, an unnamed, non-patented, seedling, and the male pollen parent, also an unnamed, non-patented, seedling.

The two parents were crossed during the summer of 2003 and the resulting seeds were planted in a controlled environment in Fredensborg, Denmark. The new variety, named 'Poulcy016', originated as a single seedling from the stated cross.

The new variety may be distinguished from its female seed parent by growth habit. The female seed parent has a spreading compact habit while the claimed plant has a climbing habit.

The new variety may be distinguished from its male pollen parent by flower color. While the claimed plant has dark red flowers, the male pollen parent has orange red flowers.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Exceptional disease resistance.
4. Reduced apical dominance in flowering habit. The new variety consistently produces flowers evenly from the lower branches to the top of the plant.

This combination of qualities is not present in previously available commercial cultivars of this type, known to the inventor, and distinguish 'Poulcy016' from all other varieties of which we are aware.

As part of the rose development program, Mogens N. Olesen germinated the seeds from the aforementioned hybridization during winter of 2003 and conducted evaluations on the resulting seedlings in a controlled environment in Fredensborg, Denmark. 'Poulcy016' was selected in the spring of 2004 by the inventor as a single plant from the progeny of the aforementioned hybridization.

Asexual reproduction of 'Poulcy016' by traditional budding and rooted cuttings was first done by Mogens N. Olesen in the nursery in Fredensborg, Denmark in July, 2004. This initial and other subsequent asexual propagations conducted in controlled environments have demonstrated that the characteristics of 'Poulcy016' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcy016'.

Specifically illustrated in FIG. 1 of the drawings are flowers at various stages of development, flower in parts, leaves, and stems.

Figure 1:
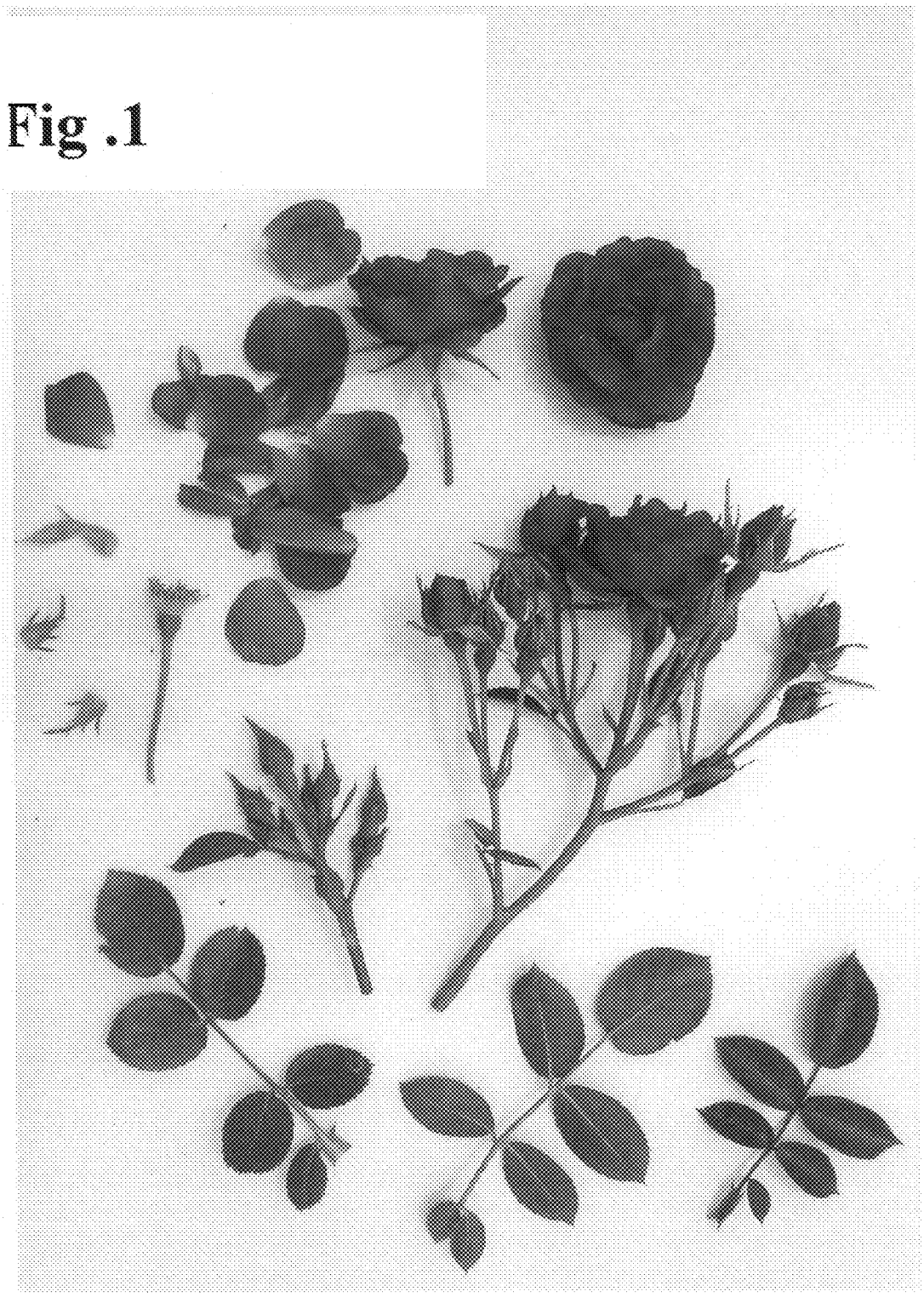
Figure 2:
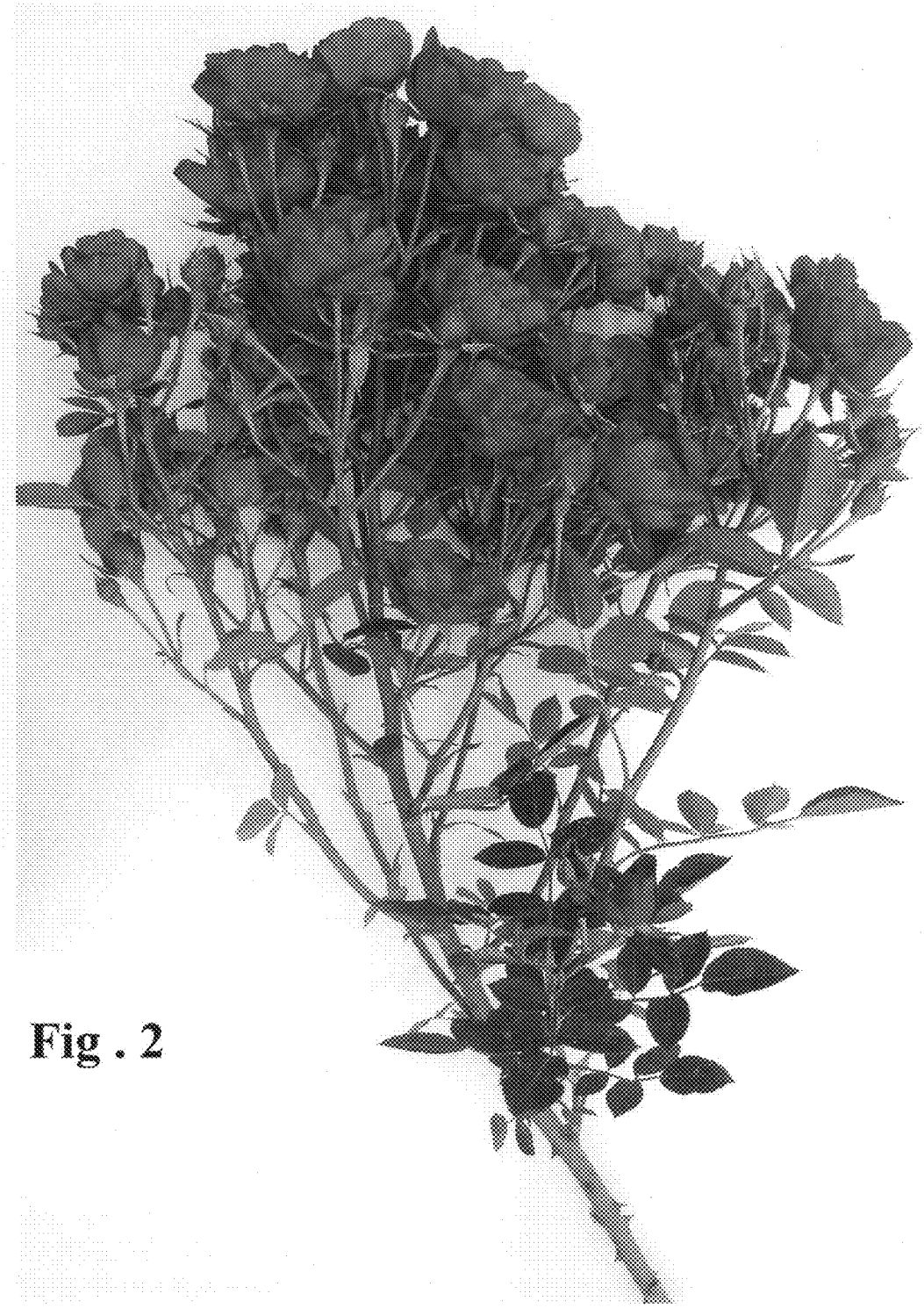

Illustrated in FIG. 2 is a cluster of open flowers on a branch.

Plants shown in the drawings are 2 years of age.

DETAILED DESCRIPTION OF THE VARIETY

The following is a description of 'Poulcy016', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcy014', described an illustrated in U.S. Plant Pat. No. 24,695, are compared to 'Poulcy016' in Chart 1.

CHART 1

| | 'Poulcy016' | 'Poulcy014' |
|---|---|---|
| Petal Count | 30 to 35 | 90 |
| Flower Diameter | 50 mm | 70-80 mm |
| General Tonality of Flower Color | Red Group 46A | Red Group 45A |

Flower and Flower Bud

Blooming habit: Continuous.

Flower bud:

*Size.*—Upon opening, 20 mm in length from base of receptacle to end of bud. Bud diameter is 9 mm.

*Bud form.*—Ovoid.

*Bud color.*—As sepals divide petals are Greyed-Purple Group 183A.

*Sepal inner surface.*—Color: Yellow-Green Group 144A. Surface: Smooth, moderately pubescent.

*Sepal outer surface.*—Color: Yellow-Green Group 144A with light intonations of Greyed-Orange Group 166B. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—20 mm long by 7 mm wide.

*Receptacle.*—Texture: Smooth. Size: 7 mm in height by 5 mm wide. Color: Yellow-Green Group 144A with intonations of Greyed-Orange Group 166B. Shape: Elliptical.

*Pedicel.*—Surface: Somewhat rough with stipitate glands. Length: 35 to 40 mm. Diameter: 2 to 3 mm on average. Color: Yellow-Green Group 144B with intonations of Greyed-Red Group 178A. Strength: Strong.

*Peduncle.*—Length: 5 to 25 cm. Diameter: 5 mm. Color: Yellow-Green Group 144A.

Flower bud development: Flower buds are borne in clusters of 5 to 11 flower buds on each individual corymb. Reduced apical dominance in flower habit causes peduncles to develop evenly from axillary buds at the base of the plant to the upper branches.

Flower bloom:

*Fragrance.*—Moderate rose scent.

*Duration.*—The blooms have a duration on the plant of approximately 7 to 10 days. Petals fall cleanly away from plant after flowers have fully matured.

*Size.*—Flower diameter is 50 mm when open. Flower depth is 20 mm.

*Flower shape.*—Semi-double. General shape is an open cup.

*Shape of flower, side view.*—The upper portion is flat. The lower portion is a flattened convex.

Petalage: Under normal conditions, flowers have 30 to 35 petals total, 7 of which are petaloids.

General tonality of flower: Open flowers are Red Group 46A.

Petal color:

*Upon and after opening, outer and inner petals.*—Upper surface: Red Group 46A with a basal petal spot color of Greyed-Yellow Group 162C at the base. Lower surface: Red-Purple Group 60B with a basal petal spot color of Greyed-White Group 156D at the base.

Petals:

*Petal reflex.*—Somewhat reflexed.

*Margin.*—Entire and uniform with a slight point at the center of the margin. No undulations of margin observed.

*Shape.*—Elliptical.

*Apex shape.*—Rounded.

*Base shape.*—Acute.

*Size.*—30 mm (l) 23 mm (w).

*Texture.*—Smooth on both the under and upper surfaces.

*Thickness.*—Average.

Petaloids:

*Size.*—20 mm (l) by 12 mm (w).

*Shape.*—Elliptic with a rounded apex and acute base shape.

*Color.*—Upper surface is Red Group 46A with a spot of Greyed-Yellow Group 162C at the base. The under surface is Red-Purple Group 60B with a spot of Greyed-White Group 156D at the base.

Reproductive organs:

*Pollen.*—None observed.

*Anthers.*—Size: 2 mm in length. Color: Greyed-Orange Group 166B. Quantity: 35 on average.

*Filaments.*—Color: Yellow Group 9A. Length: 5 mm.

*Pistils.*—Length: 4 mm. Quantity: on average.

*Stigmas.*—Color: Yellow-White Group 159C.

*Styles.*—Color: Red Group 46C.

*Location of stigmas.*—Inferior in location relative to the length of the filaments and the height of the anthers.

*Hips.*—None Observed.

Plant

Plant growth: Bushy and climbing. Plants are 100 cm in height, and 80 cm wide.

Stems:

*Color.*—Juvenile growth: Yellow-Green Group 144A. Mature growth: Yellow-Green Group 144A.

*Length.*—On average, canes are 20 to 30 cm from the base of the plant to the flowering portion.

*Diameter.*—10 mm.

*Internodes.*—On mature canes, there is an average distance of 45 mm between nodes.

*Surface texture.*—Young wood: Small prickles. Older wood: Smooth.

Long prickles:

*Incidence.*—9 prickles per 10 cm of stem.

*Size.*—Average length of prickles on mature stems is 9 mm.

*Shape.*—Upper portion is linear. Lower portion is concave.

*Color.*—Juvenile prickles: Greyed-Red Group 180A. Mature prickles: Greyed-Red Group 178A.

Plant foliage:

*Compound leaf.*—110 mm (l)×65 (w).

*Quantity.*—2 leaves per 10 cm of stem on average.

*Color of juvenile foliage*.—Upper side: Yellow-Green Group 146A. Lower side: Yellow-Green Group 146B.

*Color of mature foliage*.—Upper side: Yellow-Green Group 147A. Lower side: Yellow-Green Group 147B.

Plant leaves and leaflets:

*Stipules*.—Size: 20 mm in length. Quantity: 2 per compound leaf. Shape: Linear, slightly broad based with outward extending apices. Margins: Finely serrated. Color: Yellow-Green Group 144A.

*Petiole*.—Length: 35 mm. Diameter: 1 mm.

*Upper surface*.—Color: Yellow-Green Group 144A.

*Lower surface*.—Color: Yellow-Green Group 144A.

*Rachis*.—Length: 45 mm. Upper surface: Color: Yellow-Green Group 144A. Juvenile foliage have anthocyanin the color of Greyed-Red Group 181A.

*Lower surface*.—Color: Yellow-Green Group 144A.

*Leaflet*.—Quantity: Normal number of leaflets leaves in middle of the stem is 7 leaflets. Margins: Serrated. Size: Average size of the terminal leaflet on normal leaves is 40 mm in length by 26 mm wide. Shape: Generally ovate. Base: Rounded. Apex: Mucronate. Texture: Smooth on both the under and upper surfaces. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticultural Society heat zone 7.

The invention claimed is:

1. A new and distinct variety of rose plant of the Climbing rose class named 'Poulcy016', substantially as illustrated and described herein, due to its abundant red flowers, disease resistance, and extended period of bloom.

* * * * *